United States Patent [19]

Wang

[11] Patent Number: 5,332,828

[45] Date of Patent: Jul. 26, 1994

[54] PROCESS FOR THE PREPARATION OF BIS (2-BENZOXAZOLYL) STILBENES

[75] Inventor: Richard H. S. Wang, Kingsport, Tenn.

[73] Assignee: Eastman Kodak Company, Rochester, N.Y.

[21] Appl. No.: 20,914

[22] Filed: Feb. 22, 1993

[51] Int. Cl.$^5$ .................................. C07D 263/54
[52] U.S. Cl. ........................................... 548/219
[58] Field of Search ........................ 548/220, 219

[56] References Cited

U.S. PATENT DOCUMENTS

| | | |
|---|---|---|
| 3,366,575 | 1/1968 | Ono et al. .................. 252/301.2 |
| 3,412,089 | 11/1968 | Ohkawa et al. . |
| 3,585,208 | 6/1971 | Rash et al. .................... 548/217 |
| 3,586,673 | 6/1971 | Bloom et al. .................. 548/220 |
| 3,768,042 | 7/1972 | Matter .......................... 548/220 |
| 4,048,185 | 9/1977 | Pintschovins et al. ......... 548/220 |
| 4,282,355 | 8/1981 | Erckel et al. . |
| 4,291,964 | 5/1990 | Bowers, Jr. et al. .......... 548/219 |

Primary Examiner—Donald G. Daus
Attorney, Agent, or Firm—J. Frederick Thomsen

[57] ABSTRACT

Disclosed is an improved process for the preparation of 4,4'-bis(2-benzoxazolyl)stilbene compounds by the reaction of 4,4'-stilbenedicarboxylic acid with 2-aminophenol compounds in the presence of a tin or titanium catalyst and certain solvents.

3 Claims, No Drawings

PROCESS FOR THE PREPARATION OF BIS (2-BENZOXAZOLYL) STILBENES

This invention pertains to the preparation of 4,4'-bis(2-benzoxazolyl)stilbene compounds by the reaction of 4,4'-stilbenedicarboxylic acid with 2-aminophenol compounds in the presence of a tin or titanium catalyst and certain solvents.

Unsubstituted and substituted 4,4'-bis(2-benzoxazolyl)stilbene compounds are known compositions of matter which are useful as optical brightening or whitening agents in various polymeric materials, particularly fiber-forming, synthetic polymers. U.S. Pat. No. 4,921,964 discloses the preparation of bis(2-benzoxazolyl)stilbene compounds by the reaction of dialkyl stilbenedicarboxylate ester with various 2-aminophenol compounds in the presence of certain solvents and catalysts. U.S. Pat. No. 3,412,089 teaches that the use of 4,4'-stilbenedicarboxylic acid in preparing 4,4'-bis(2-benzoxazolyl)stilbene compounds generally does not give satisfactory results because of the high melting point of the diacid and its limited solubility in many solvents. The '089 patent discloses that 4,4'-stilbenedicarboxylic acid may be used in the preparation of 4,4'-bis(2-benzoxazolyl)stilbene compounds by the reaction thereof with certain 2-aminophenols using a substantial amount of powerful phosphoric acid dehydrating agents such as pyrophosphoric and polyphosphoric acids as the reaction medium. Other known process which employ 4,4'-stilbenedicarboxylic acid first convert the diacid to its diacid dichloride using chlorinating agents such as thionyl chloride, phosphorus oxychloride and phosphorus trichloride. Both the phosphoric acid dehydrating agents or the chlorinating agents are highly corrosive requiring the use of equipment fabricated of corrosion resistant materials. Furthermore, the use of such dehydrating and chlorinating agents require the subsequent use of a basic material.

I have discovered that 4,4'-bis(2-benzoxazolyl)stilbene compounds may be obtained in good purity and yields by a simple, one-step process wherein 4,4'-stilbenedicarboxylic acid is reacted with 2-aminophenol compounds in the presence of a tin or titanium catalyst and certain solvents. The present invention therefore provides a process for the preparation of 4,4'-bis(2-benzoxazolyl)stilbene compounds having the formula

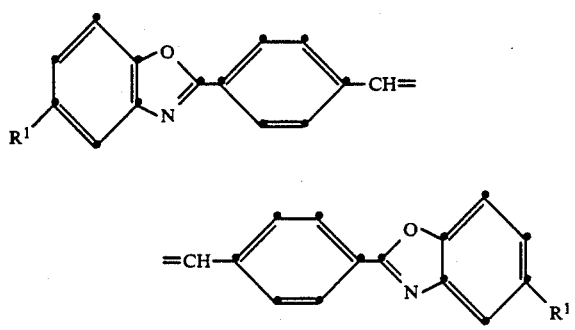

which comprises reacting 4,4'-stilbenedicarboxylic acid with one or more 2-aminophenol compounds having the formula in the presence of a tin or titanium catalyst and an inert organic solvent having a boiling point above 200° C., wherein each $R^1$ is independently selected from hydrogen, alkyl of up to about 12 carbon atoms and alkoxy of up to about 12 carbon atoms. $R^1$ preferably represents hydrogen or alkyl of up to about 4 carbon atoms, especially methyl. The 4,4'-bis(2-benzoxazolyl)stilbene products may be isolated by filtration in a purity which is sufficient for use without further purification.

Examples of the inert, organic solvents which may be used include naphthalene; alkyl-substituted naphthalene compounds such as methylnaphthalene and dimethylnaphthalenes; halogenated naphthalenes such as chloronaphthalene; biphenyl; aromatic ethers such as diphenylether; aromatic alkanes such as diphenylethane; and the like. Alkyl-substituted naphthalenes containing a total of 11 to 20 carbon atoms represent the preferred solvents. The amount of solvent employed is not important. However, the weight ratio of the solvent to the total weight of the 4,4'-stilbenedicarboxylic acid with 2-aminophenol reactants typically will be in the range of 2:1 to 10:1.

The process typically is carried out over a temperature range of about 200° to 300° C., preferably 220° to 260° C. Pressure normally is not an important process condition and the process therefore normally is performed at ambient pressure or moderately elevated pressure generated in a sealed reactor, i.e., autogenous pressures.

The organo-tin and organo-titanium catalyst compounds useful in my novel process are well known esterification, polyesterification, alcoholysis, and acidolysis catalysts. These compounds are described in U.S. Pat. No. 3,585,208 and references cited therein. The prepared organo-titanium compounds are titanium alkoxides containing a total of up 20 carbon atoms, preferably 4 to 16 carbon atoms. Titanium tetraisopropoxide and acetyltitanium triisopropoxide are specific examples of suitable organo-titanium catalysts. The organo tin compounds may be selected from dihydrocarbyltin oxides such as dibutyltin oxide. The amount of the organo-titanium and organo-tin catalysts which may be used normally is in the range of about 5 to 20 mole percent based on the moles of 4,4'-stilbenedicarboxylic acid present.

The process of the present invention is further illustrated by the following examples.

EXAMPLE 1

A mixture of 4,4'-stilbenedicarboxylic acid (13.4 g, 0.05 mole), 2-aminophenol (12.5 g, 0.115 mole), titanium tetraisopropoxide (2.0 mL) and methylnaphthalene (100 ml) was heated in a 300 mL, 3-necked flask for 1 hour at each of the temperatures: 220° C., 230° C., 240° C., 250° C., and 260° C. The low boilers were distilled off continuously at less than 100° C. After the reaction mixture was cooled to 150° C., xylene (100 mL) was added with stirring. The product was collected by filtration at 80° C., washed with warm xylene (4×50 mL), methanol (2×50 mL), and acetone (2×50 mL), the pure product, bis-(2-benzoxazolyl)stilbene, was obtained in 95% yield.

EXAMPLE 2 AND 3

The procedure of Example 1 was repeated using equimolar amounts of 2-amine-4-methylphenol and 2-amino-4-tertiary butylphenol to obtain 4,4'-bis(5-methyl-2-benzoxazolyl)stilbene and 4,4'-bis(5-t-butyl-2-benzoxazolyl)stilbene in yields of 90 to 95%.

The invention has been described in detail with particular reference to preferred embodiments thereof, but it will be understood that variations and modifications can be effected within the spirit and scope of the invention.

I claim:

1. Process for the preparation of 4,4'-bis(2-benzoxazolyl)stilbene compounds having the formula

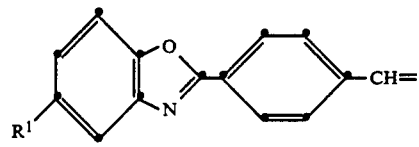

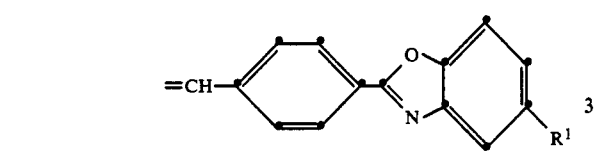

which comprises the step of reacting 4,4'-stilbenedicarboxylic acid with one or more 2-aminophenol compounds having the formula in the presence of a tin or titanium catalyst and an inert organic solvent having a boiling point above 200° C. selected from alkyl-substituted naphthalenes having 11 to 20 carbon atoms, wherein each R$^1$ is independently selected from hydrogen, alkyl of up to 12 carbon atoms and alkoxy of up to 12 carbon atoms.

2. Process according to claim 1 performed at a temperature in the range of 220° to 260° C.

3. Process for the preparation of 4,4'-bis(2-benzoxazolyl) stilbene compounds having the formula

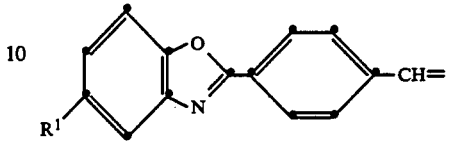

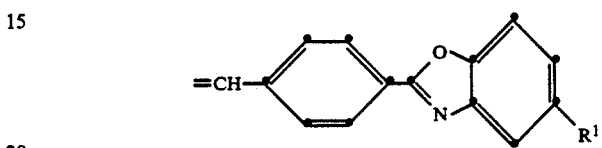

which comprises the step of reacting 4,4'-stilbenedicarboxylic acid with one or more 2-aminophenol compounds having the formula

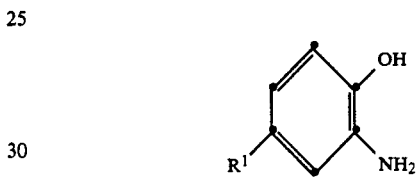

a temperature in the range of 220° to 260° C. in the presence of a titanium alkoxide catalyst and an inert organic solvent having a boiling point above 200° C. selected form alkyl-substituted naphthalenes having 11 to 20 carbon atoms, wherein each R$^1$ is independently selected from hydrogen and alkyl of up to 4 carbon atoms.

* * * * *

UNITED STATES PATENT AND TRADEMARK OFFICE
CERTIFICATE OF CORRECTION

PATENT NO. : 5,332,828
DATED : July 26, 1994
INVENTOR(S) : Wang

It is certified that error appears in the above-indentified patent and that said Letters Patent is hereby corrected as shown below:

Column 3, line 36 (Claim 1), after "having the formula" insert

--- 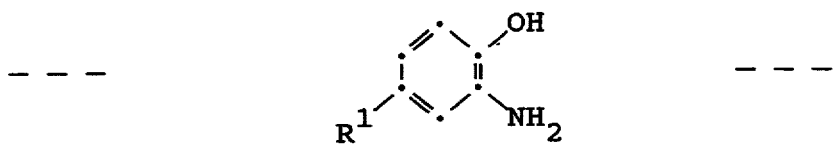 ---

Column 4, line 33 (Claim 3), should read "at a temperature in. . . .".

Column 4, line 36 (Claim 3), "form" should be "from".

Signed and Sealed this

Eleventh Day of October, 1994

Attest:

BRUCE LEHMAN

*Attesting Officer*   *Commissioner of Patents and Trademarks*